(12) United States Patent
Neuberger

(10) Patent No.: US 6,485,414 B1
(45) Date of Patent: Nov. 26, 2002

(54) COLOR VIDEO DIAGNOSTIC SYSTEM FOR MINI-ENDOSCOPES

(75) Inventor: Wolfgang Neuberger, Labuan (MY)

(73) Assignee: CeramOptec Industries, Inc., East Longmeadow, MA (US)

(*) Notice: Subject to any disclaimer, the term of this patent is extended or adjusted under 35 U.S.C. 154(b) by 0 days.

(21) Appl. No.: 09/525,625

(22) Filed: Mar. 14, 2000

Related U.S. Application Data

(63) Continuation-in-part of application No. 09/114,610, filed on Jul. 13, 1998, now abandoned.

(51) Int. Cl.[7] .................................................. A61B 1/07
(52) U.S. Cl. ........................ 600/182; 600/178; 600/108
(58) Field of Search ................................ 660/108, 160, 660/178, 180, 182, 407, 473, 478

(56) References Cited

U.S. PATENT DOCUMENTS

| | | | |
|---|---|---|---|
| 4,261,344 A | | 4/1981 | Moore et al. |
| 4,383,729 A | * | 5/1983 | Suzuki et al. ................ 128/898 |
| 4,653,478 A | | 3/1987 | Nagasaki et al. |
| 4,770,653 A | * | 9/1988 | Shturman .................... 600/108 |
| 5,144,689 A | * | 9/1992 | Lovely .................. 250/227.19 |
| 5,166,787 A | * | 11/1992 | Irion ............................ 348/75 |
| 5,419,312 A | * | 5/1995 | Arenberg et al. ........... 600/108 |
| 5,512,034 A | * | 4/1996 | Finn et al. ................... 600/138 |
| 5,569,239 A | * | 10/1996 | Sinofsky ...................... 128/898 |
| 5,657,165 A | | 8/1997 | Karpman et al. |
| 5,701,902 A | * | 12/1997 | Vari et al. .................... 600/473 |
| 5,810,719 A | * | 9/1998 | Toida ........................... 356/495 |

* cited by examiner

*Primary Examiner*—John P. Leubecker
(74) *Attorney, Agent, or Firm*—Bolesh J. Skutnik; BJ Associates

(57) ABSTRACT

A color video diagnostic system for mini-endoscopes for viewing features of objects where access to the object is limited or where minimally invasive techniques are preferable, such as in medical or industrial applications. A black-and-white video chip mounted at the distal end of an endoscope body images an object sequentially illuminated by laser diode light sources having different wavelengths. More than one laser diode may be used within a color region to provide truer color representations. A controller controls the laser diode light sources for sequentially illuminating the object by color, and a video processor responsive to the controller receives signals from the black-and-white video chip for producing a color data signal. A display displays a color image of the object. At least one diagnostic laser diode light source, which can be tunable, may be included for enhancing selected features of the object being viewed, and it may emit in the visible, near infrared, or infrared wavelength regions. A beam-combining element can be included for combining the light beams from the laser diode light sources for provision to a fiber light transport element for transporting the light to illuminate the object.

16 Claims, 2 Drawing Sheets

COLOR VIDEO DIAGNOSTIC SYSTEM FOR MINI-ENDOSCOPES

REFERENCE TO RELATED CASE

This application is a continuation-in-part of U.S. patent application Ser. No. 09/114,610 filed on Jul. 13, 1998 by Wolfgang Neuberger, inventor entitled "COLOR VIDEO DIAGNOSTIC SYSTEM FOR MINI-ENDOSCOPES", now abandoned, and incorporated by reference herein.

BACKGROUND OF THE INVENTION

1. Field of the Invention

This invention relates to a diagnostic and inspection system for viewing objects where access to the object is limited such as where minimally invasive techniques are preferable, and more particularly to a diagnostic color video system for medical and/or industrial applications needing miniature endoscopes, i.e. diameter at the distal end of less than 2 mm.

2. Informational Disclosure Statement

Endoscopes have many industrial applications and medical applications, and are typically used to access and view objects located within apparati or bodies. In an industrial application, an endoscope, generally called a borescope, may be used to view the hidden components of an internal combustion engine; in a medical application, an endoscope may be used for minimally invasive viewing for diagnosis. A medical endoscope can also be used in conjunction with the delivery of drugs to, or other treatment at a specific site or with the cutting or ablation of diseased or damaged tissue.

An endoscope typically includes a body having a distal end for insertion and image collection; a lumen or passage for conveying wiring, an optical waveguiding element for conveying light, (e.g. optical fibers) and perhaps mechanical cables to the distal end; and a proximate end for manipulation by the operator and for access to the elements carried to the distal end.

Optimally, an endoscope is small and lightweight such that the distal end can be easily inserted into narrow internal passages and can be readily positioned by manipulation of the proximate end; flexible, such that the endoscope body readily follows the contours of internal passages; capable of manufacture at reasonable cost; and capable of collecting considerable diagnostic information. In practice, designing an endoscope that incorporates all of the above features can be difficult. Standard endoscopes for medical applications typically have 3 mm outer diameter with newer ones lying in the range of 2–3 mm. Industrial endoscopes currently are generally larger in diameter.

For example, an endoscope typically illuminates the object to collect an image thereof. Accordingly, powerful light sources conveying light over large diameter (i.e., low-loss) fiber bundles, large collection optics and large diameter coherent fiber bundles for conveying the collected image from the distal to the proximate end of the endoscope are commonly used in standard endoscopes. In many cases, the required maneuverability and flexibility dictate that the illumination fiber bundle has large numbers of small diameter fibers, and that the imaging fiber optic bundle likewise uses large numbers of small diameter fibers. Large numbers of small fibers are normally required because smaller dimensioned fibers result in higher loss. Using many small diameter fibers thus provides flexibility but the fiber bundle remains large because of their higher loss, which would reduce illumination. Additionally, while small diameter fibers can improve resolution in the image bundle, the manufacture of the coherent bundle becomes more complex as the number of individual fibers increases.

A color image can convey more diagnostic information than a black-and-white image. However, bulkier, more sophisticated and more expensive signal processing hardware is typically associated with producing a color image.

Prior attempts are documented in patents such as U.S. Pat. No. 4,653,478 issued to Nagasaki et al., and U.S. Pat. No. 4,261,344 issued to Moore et al. In these approaches, a charge coupled device (CCD) positioned at the distal end of the endoscope converts the image of the object to electrical impulses, which are transmitted within the body of the endoscope by wires that are less bulky than fibers carrying the image. A color image is obtained from the device by sequentially illuminating the object with light obtained by sequentially placing appropriate filters in front of a white light source. Multiplexing the image data creates an RGB sequence. Full-color video pictures are thus obtained.

Disclosed in each of these patents, however, are standard multi-wavelength light sources, which either use filters to select a broad color region or colored light sources. For example in the Nagasaki et al. patent, the choice of sources are; a white light with appropriate color filters to get sequential RGB illumination, or red, green and blue lamps, or alternatively illuminous diodes, emitting light of the 3 primary colors. In the Moore patent, bulky strobe light sources convey light to the object via separate bundles of fibers, thus reducing the maneuverability and flexibility of the endoscope. Each of the colored light sources, including the filtered white light, emits and transmits a relatively broad distribution of wavelengths within the specified color region to the distal end of the endoscope. This is good in terms of reconstitution for true color vision, but these sources are generally of moderate power intensity, at best. The transmission elements, connecting light source to illuminated site, need to contain large core fibers or very large numbers of small core optical fibers to allow sufficient energy density to be seen and recorded. The only alternative to these schemes, is that Nagasaki et al. suggests that illuminous diodes could be used directly attached to the side of the detector chip. This would likely keep the tip larger than might be preferred and also, for the medical applications, could leasd to introducing metals and semimetals to the patient's body that would best be kept away from body tissues and fluids.

The prior art would not recommend using laser sources for color video systems, even though they have high brightness, because a laser normally emits a very limited number of wavelengths around its main operating wavelength, i.e. possibly 2–5 nm or less about the operating wavelength, giving a specific shade of red rather merely red. Luminous diodes in contrast can produce broad enough light to span the blue-green region of the spectrum as described in U.S. Pat. No. 5,657,165 issued to Karpman, so that sequential filtering with blue and green filters can be employed to project blue and then green beams, respectively.

Accordingly, as an improved endoscope would be a useful and welcome advance, it is an object of the present invention to address one or more of the aforementioned drawbacks and disadvantages of the prior art.

Other general and specific objects of the invention will in part be apparent and will in part appear hereinafter.

OBJECTS AND SUMMARY OF THE INVENTION

It is an object of the present invention to provide a color video diagnostic system for mini-endoscopes having a black-and-white video chip for collecting an image of the object being viewed and a laser diode illumination source for providing different colors of light for illuminating the object.

It is another object of the present invention to include a diagnostic laser diode light source having a wavelength selected for fluorescing an imaging agent for imaging a selected feature of an object being viewed. The object is exposed to an imaging agent, which is selected to target a specific feature of the object and which is known to be excited by a predetermined wavelength of light to fluoresce. The diagnostic laser diode light source is selected to operate at the predetermined wavelength, which may be within the near infrared spectral region. The feature, if part of the object, can be more readily distinguished on the video display of the color signal.

Briefly stated, the present invention provides a color video diagnostic system for mini-endoscopes for viewing features of objects where access to the object is limited or where minimally invasive techniques are preferable, such as in medical or industrial applications. A black-and-white video chip mounted at the distal end of an endoscope body images an object sequentially illuminated by laser diode light sources having different wavelengths. More than one laser diode may be used within a color region to provide truer color representations. A controller controls the laser diode light sources for sequentially illuminating the object by color, and a video processor responsive to the controller receives signals from the black-and-white video chip for producing a color data signal. A display displays a color image of the object. At least one diagnostic laser diode light source, which can be tunable, may be included for enhancing selected features of the object being viewed, and it may emit in the visible, near infrared, or infrared wavelength regions. A beam-combining element can be included for combining the light beams from the laser diode light sources for provision to a fiber light transport element for transporting the light to illuminate the object.

The invention thus advantageously incorporates laser diode light sources, which have exceptional brightness, particularly when diode lasers or diode pumped solid state lasers or directly frequency doubled laser diodes are employed with a black-and-white video chip, that is less expensive and bulky than a color video chip, to provide an improved endoscope. The brightness of the laser diode sources, as well as the beam combiner, allow use of a fiber transport element having fewer optical fibers with at most one per laser source, thereby reducing the diameter of the fiber 'bundle' and of the outer casing for the system and enhancing the flexibility of the endoscope. In one embodiment, the fiber light transport element can be a single optical fiber.

Incorporation of the diagnostic laser diode light source thus advantageously provides a more versatile mini-endoscope with increased diagnostic capabilities, without adding significant bulk or weight to the mini-endoscope, thus maintaining maneuverability and ease of use.

These and other features of the invention are more fully set forth below.

BRIEF DESCRIPTION OF THE DRAWINGS

For a more complete understanding of the invention, reference is to be made to the following Detailed Description of the Preferred Embodiments and the accompanying drawings, in which.

DETAILED DESCRIPTION OF THE PREFERRED EMBODIMENTS

Figure 1:
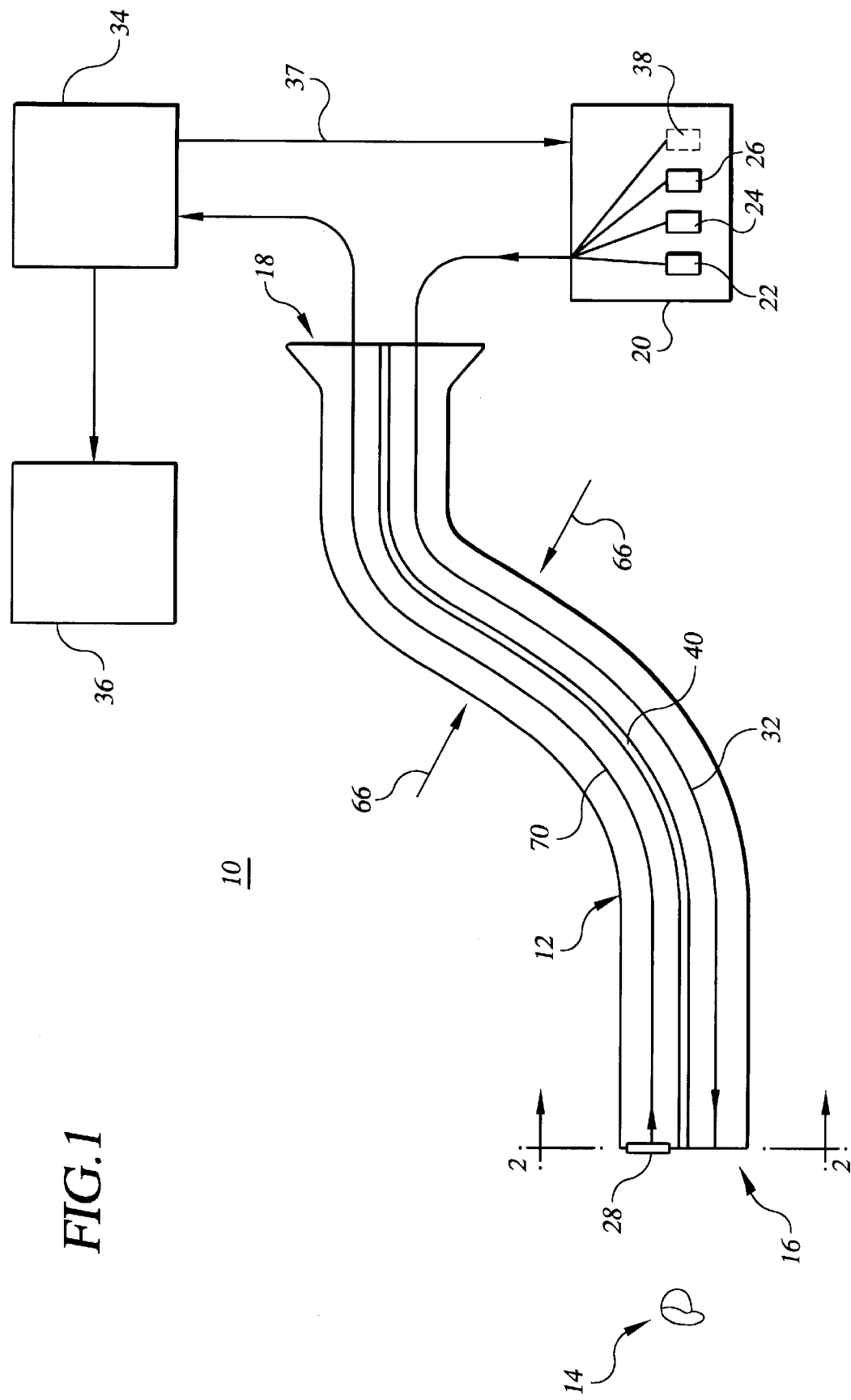
FIG. 1 is a schematic illustration of a color video diagnostic system for mini-endoscopes according to the present invention.

FIG. 1 illustrates generally mini-endoscope 10 according to the present invention, with endoscope body 12 illustrated as positioned for viewing object 14. Endoscope body 12 includes distal, or viewing, end 16 and proximate end 18. Laser diode illumination source 20 provides at least three colors of light, typically emanated by three laser diode light sources, 22, 24 and 26 respectively, each of a different color. Black-and-white video chip 28 is located approximately at distal end 16 of endoscope body 12 for receiving an image of object 14. The term "laser diode light source," as used herein, can include, but is not limited to, laser diodes, frequency-doubled laser diodes, diode pumped solid state lasers, frequency-doubled diode pumped solid state lasers, diode pumped fiber lasers, diode laser pumped optical parametric oscillators, and tapered diode lasers. Fiber light transport element 32 conveys light from laser diode illumination source 20 to distal end 16 of endoscope body 12, where the light is radiated to illuminate object 14.

Video processor/controller 34 controls laser diode light sources 22, 24 and 26 to sequentially illuminate object 14 with light from each laser diode light source, and processes image data received from black-and-white video chip 28 to generate a color video signal for displaying a color image of object 14 on video display 36. Reference numeral 37 indicates control of laser diode light sources 22–26 by video processor/controller 34. One technique for using sequential illumination to produce a color display on an ordinary television receiver, using processes compatible with standard format television, is disclosed in U.S. Pat. No. 4,261,344 issued to Moore et al. and herein incorporated by reference. Other useful video imaging techniques, such as disclosed in Nagasaki et al. in U.S. Pat. No. 4,653,478 or developed in conjunction with the advent of powerful, compact and affordable digital computers, can readily be envisioned as appropriate by one of ordinary skill in the art in light of the disclosure herein.

The colors of laser diode light sources 22–26 are selected for illuminating object 14 to produce a color image. For example, red, green and blue light can be used to compose a color image. Other colors can also be used, and, as is known in the art, the separation of the colors on a chromaticity chart determines the range of color that can be displayed on video display 36.

It may also be necessary and advantageous for certain endoscope embodiments of the present invention to incorporate two or more lines of a given color, and thus more diode laser sources. This could be useful to produce truer, better contrast, and more life like color images, particularly in the blue and green ranges where the eye is more sensitive and color differences matter more, provided that the intensities of the illuminating sources and the video signal processor are properly adjusted.

Laser diode illumination source 20 can optionally include diagnostic laser diode light source 38 for enhancing selected features of object 14 for imaging and display on video display 36. Diagnostic laser diode light source 38 is selected to operate at a wavelength that fluoresces an imaging agent for imaging a feature of object 14 being viewed. It can be in the infrared or near infrared as well as in the visible range of the spectrum.

The object is exposed to the imaging agent, which is selected to target a specific feature of the object and which is known to be excited to fluoresce by a predetermined wavelength of light, which need not be only within the visible spectrum range. The specific feature, if present, can be more readily distinguished on video display 36 of the color signal. Diagnostic sources outside the visible range may require special video chips with extra sensitivity and a means to create, possibly a false color, a means for the operator to view the absorption/reflection/fluorescence of the diagnostic light.

The diagnostic imaging agent is typically a two-part imaging agent that combines an imaging moiety and a targeting moiety. For example, to highlight a cancerous tumor on object 14 on video display 36, the imaging moiety can be a fluorescent substance that covalently bonds to a targeting moiety that is an antibody that targets a tumor protein. Diagnostic laser diode light source 38 excites the imaging agent to fluoresce, thus highlighting the tumor on display 36. This example of enhancing the image of a cancerous tumor is exemplary. One of ordinary skill in the art, in light of teachings herein, can readily select diagnostic agents and colors of diagnostic laser diode light source 38 to enhance other features of objects viewed with system 10 of the present invention.

Alternatively the diagnostic laser diode light source could be selected, which emits a wavelength which can cause fluorescence in a naturally occuring compound within the field of inspection of the mini-endoscope. In this case an independent imaging agent is not needed. Targeting occurs by selecting the proper wavelength to activate the cells or object under study.

Where used, endoscope body 12 can also house interior tube 40 for delivery of a diagnostic agent to object 14, as is discussed in additional detail below. The diagnostic imaging agent need not be introduced to object 14 via interior tube 40 and can often be introduced by means entirely independent of mini-endoscope 10.

Diagnostic laser diode light source 38 can be a tunable light source for varying the wavelength of light emitted, thereby providing versatile mini-endoscope 10 capable of working with a variety of diagnostic imaging agents. For example, distributed back reflection (DBR) diode lasers and Distributed Feedback (DFB) diode lasers are known in the art and can be tuned by varying either the operating temperature or the excitation current of the laser, or both. If this tuning range is insufficient, a multiplicity of diodes with different wavelengths can be used. For example, the mini-endoscope of the present invention can be used in conjunction with a first diagnostic imaging agent for enhancing a first feature of object 14, diagnostic laser diode light source 38 being tuned for causing the first diagnostic imaging agent to fluoresce. Subsequently, a second diagnostic agent for imaging a second feature can be introduced, such as by tube 40, and diagnostic laser diode light source 38 tuned, such as by video processor/controller 34, for imaging the second feature on display 36. Video display 36 or processor/controller 34 can include a memory for storing the image of the first enhanced feature, such that the second and first enhanced features can be displayed simultaneously on display 36. Similarly it is also possible to include a Raman spectroscopic image in the display.

Alternatively, both the first and second diagnostic imaging agents can be simultaneously introduced to object 14, and video processor/controller 34 can alternatively tune the operating wavelength of diagnostic laser diode light source 38 between first and second wavelengths for sequentially fluorescing the first and second diagnostic imaging agents. As is understood by one of ordinary skill in the art, in light of the teachings herein, suitable control and processing by video processor/controller 34 can display both the first and second enhanced features on video display 36. It is also possible to overlay any of the fluorescent images to the Red/Green/Blue (RGB) video image, for example as a contour line.

Figure 2:
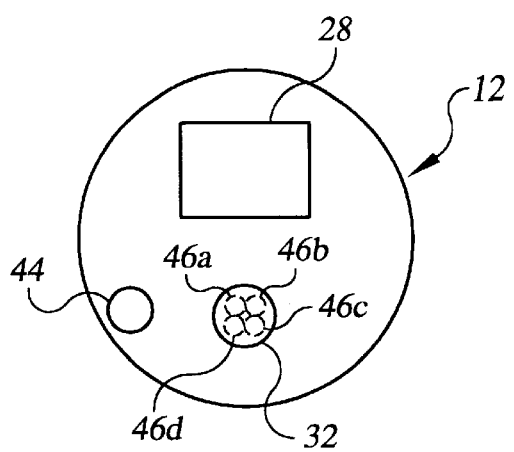
FIG. 2 is an end view taken along section line 2—2 of FIG. 1 and illustrating the distal end of the endoscope body of FIG. 1.

Shown in FIG. 2 are black-and-white video chip 28, fiber light transport element 32, and aperture 44 formed by tube 40 for delivering substances to object 14. Note that fiber light transport element 32 can include individual fibers 46a, 46b, 46c and 46d, each of which conveys light from a different one of laser diode light sources 22, 24, 26 and 38, respectively.

Figure 3:
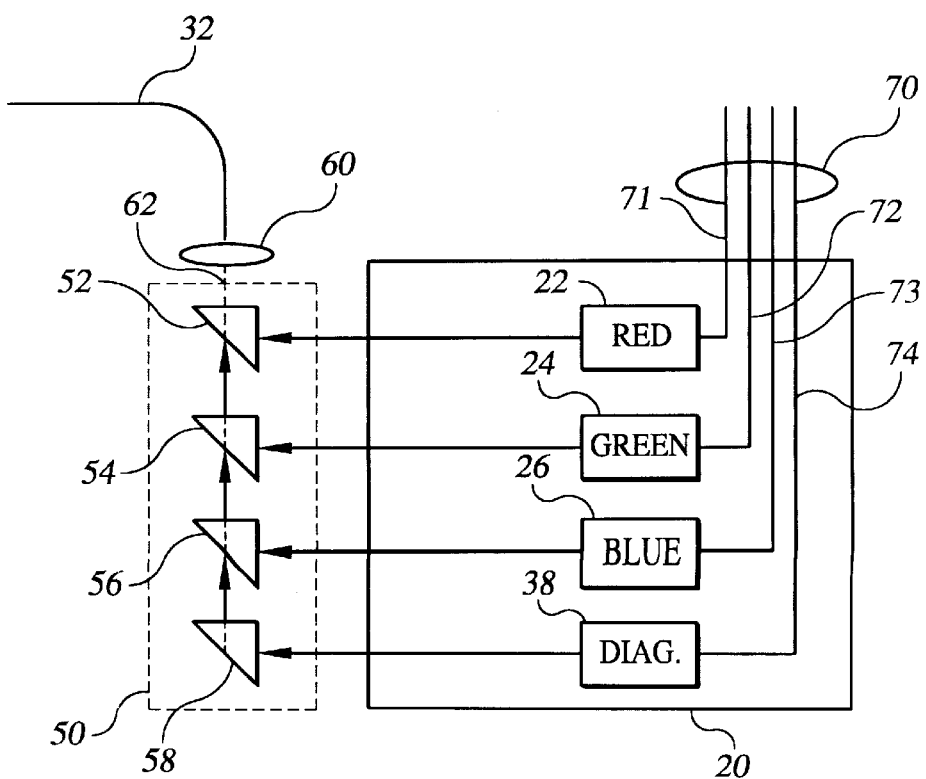
FIG. 3 is a diagram of the laser diode illumination source of FIG. 1 and a beam-combining apparatus for combining the beams from the laser diode illumination source to travel the fiber light transport element to illuminate the object being viewed.

In another embodiment of the invention, fibers 46a–46d act as a bundle such that each of individual fibers 46a–46d transport light from each of the laser diode light sources, or, if fiber transport element 32 is a single fiber, the single fiber transports all light to the distal end of endoscope body 12. Such an embodiment includes, as illustrated in FIG. 3, beam-combining element 50. Beam-combining element 50 combines the beams from laser diode light sources 22–26, and optionally from diagnostic laser diode light source 38, to travel fiber light transport element 32.

The beam-combining element 50 can include beam splitters 52–58 for combining light beams emanating from laser diode light sources 22, 24, 26 and 38 onto the fiber light transport element 32. Beam conditioning optics 60 can be included for launching beam 62 onto fiber light transport element 32.

Beam-combining element 50 thus advantageously allows a reduction in the diameter "d", referenced by numeral 66 in FIG. 1, of endoscope body 12 for enhancing the flexibility thereof. For example, the number of fibers required to convey sufficient light to object 14 may vary, although it is considered that for many applications the present invention will advantageously allow the use of fiber light transport element 32 that is a single fiber. Nevertheless, whatever the number of fibers, the use of laser diode light sources, having exceptional brightness, and/or beam-combining element 50 can reduce the need for an undue multiplicity of fibers. Beam-combining element 50 can allow the use of some fibers in common.

Preferably fiber light transport element 32 includes a single silica fiber (or individual silica fibers) having a core diameter that is less than approximately 75 μm; more preferably the core diameter of the fiber is less than approximately 60 μm; and most preferably, the core diameter is less that approximately 55 μm. A silica fiber having a core diameter of approximately 50 μm and a numerical aperture of 0.2 is also suitable. Given the rapid advances in diode laser technology, core diameters of 10 μm appear feasible in the near future. Advantageously, the fiber light transport element 32 need not include an AF Teflon® coated fiber, and is thus less expensive, than, for example, some of the fibers of the prior art. In one embodiment, fiber light transport element 32 is a single silica fiber having a core diameter according to the numerical ranges and the example described above. These core dimensions for single fibers are well below the current state of the art. Most diode laser sources are fibers with core diameters of at least 200 μm, particularly for higher power diode laser sources. Coupling light from high power diode lasers has proven to be a general problem, because of their very highly diverging emission in their fast axis direction.

FIG. 3 also illustrates further detail of control line 70 of FIG. 1 for providing communication between video processor/controller 34 and laser diode illumination source 20. As illustrated in FIG. 3, control line 70 can include individual control lines 71–74 for each laser diode light source 22, 24, 26 and 38.

Thus it is seen that the objects set forth above, among those made apparent from the preceding description, are officially attained. Because certain changes may be made in the above constructions without departing from the scope of the invention, it is intended that all matter contained in the above description and shown in the accompanying drawings be considered as illustrative and not in a limiting sense. For example, a desired diagnostic imaging agent may fluoresce in the infrared spectrum rather than the visible spectrum. Black-and-white video 28 chip can include infrared imaging capability, or an additional infrared-sensitive imaging chip can be incorporated with mini-endoscope 10 and the signal therefrom suitably processed for display on video display 36.

As another example, although reference numeral 34 of FIG. 1 indicates a single block for video processing of signals received from black-and-white video chip 28 and for controlling the sequential illumination of light sources 22–26, the use of a single block should not be taken to imply that such control and video processing need be necessarily implemented as a single integrated chip. One of ordinary skill in the art, in light of the disclosure herein, appreciates the functionality necessary to produce image on display 36, and further that such functionality can be implemented by various combinations of hardware, firmware, and software, using any number of discreet components in appropriate communication for producing the required image on display 36.

As yet another example, diagnostic laser diode light source 38 can be tunable such that it alternatively serves the function of one of laser diode light sources 22, 24 or 26, providing a wavelength for producing a color image, and the diagnostic function of causing the imaging agent to fluoresce.

Having described preferred embodiments of the invention with reference to the accompanying drawings, it is to be understood that the invention is not limited to these precise embodiments, and that various changes and modifications may be effected therein by one skilled in the art without departing from the scope or spirit of the invention as defined in the appended claims.

What is claimed is:

1. A color video diagnostic system for mini-endoscopes for viewing an object, comprising:
   an elongated body having a distal end and a proximate end;
   a black-and-white video chip mounted at approximately said distal end of said body for receiving an image of an object to be viewed;
   a laser diode illumination source including at least first, second and third laser diode light sources having different wavelengths for illuminating said object for producing a color image thereof;
   a fiber light transport element for conveying light from said light sources along said body to said distal end of said endoscope for illuminating said object;
   a controller for controlling said laser diode light sources for sequentially illuminating said object with light from said laser diode light sources;
   a video processor responsive to said controller and for receiving signals from said video chip for producing a color data signal for provision to a video display for display of a color image of said object;
   wherein said laser diode light source is selected from the group: laser diodes, frequency-doubled laser diodes, diode pumped solid state lasers, frequency-doubled diode pumped solid state lasers, diode pumped fiber lasers, diode laser pumped optical parametric oscillators, and tapered diode lasers; and
   wherein said fiber light transport element is at most one optical waveguide per diode laser source and said optical waveguides have a core dimension no greater than 75 μm.

2. The color video diagnostic system for mini-endoscopes of claim 1 further including a beam-combining element for combining light beams from at least two of said at least first, second and third laser diode light sources for provision to said fiber light transport element.

3. The color video diagnostic system for mini-endoscopes of claim 1 further including a beam-combining element for combining light beams from said at least first, second and third laser diode light sources for provision to said fiber light transport element, and wherein said fiber light transport element is a single silica optical fiber.

4. The color video diagnostic system for mini-endoscopes of claim 3, wherein said single optical fiber has a core diameter no greater than 60 μm.

5. The color video diagnostic system for mini-endoscopes of claim 1 wherein said laser diode illumination source includes at least one diagnostic laser diode light source for enhancing a selected feature of said object viewed by said mini-endoscope.

6. The color video diagnostic system for mini-endoscopes of claim 5 wherein said at least one diagnostic laser diode light source includes a tunable diode laser.

7. The color video diagnostic system for mini-endoscopes of claim 5 wherein said at least one diagnostic laser diode light source includes a diode laser pumped optical parametric oscillator.

8. The color video diagnostic system for mini-endoscopes of claim 1 wherein said laser diode illumination source includes at least one diagnostic laser diode light source for enhancing a selected feature of the object being viewed, and wherein said system also includes a beam-combining element for light beams from said at least first, second and third laser diode light sources and said at least one diagnostic laser diode light source for provision to said fiber light transport element.

9. The color video diagnostic system for mini-endoscopes of claim 8 wherein said fiber light transport element is at least one optical fiber.

10. The color video diagnostic system for mini-endoscopes of claim 9, wherein said single optical fiber has a core diameter no greater than 60 μm.

11. The color video diagnostic system for mini-endoscopes of claim 8 wherein said at least one diagnostic laser diode light source is a tunable diode laser.

12. A color video diagnostic system for mini-endoscopes for viewing an object, comprising:
   an elongated body having a distal end and a proximate end;
   means mounted at approximately said distal end of said body for receiving an image of said object to be viewed and for producing a black-and-white video signal;

a laser diode illumination source including at least first, second and third laser diode light sources having different wavelengths for producing light beams for illuminating said object to produce a color image thereof;

optical waveguide means for transmitting said light beams from said laser diode illumination source to said distal end of said elongated body for illuminating said object;

means for combining light beams from at least two of said at least first, second and third laser diode light sources for provision to said optical waveguide means;

means for controlling said laser diode light sources for sequentially illuminating said object with light from said laser diode light sources;

video processor means responsive to said controller and to said black-and-white signals from said video chip for producing a color data signal;

display means for receiving said color data signal and for displaying a color image of said object;

wherein said laser diode light source is selected from the group: laser diodes, frequency-doubled laser diodes, diode pumped solid state lasers, frequency-doubled diode pumped solid state lasers, diode pumped fiber lasers, diode laser pumped optical parametric oscillators, and tapered diode lasers; and wherein said optical waveguide means is not more than one optical waveguide per laser source and each waveguide has a core dimension no greater than 75 μm.

13. The color video diagnostic system for mini-endoscopes of claim 12 wherein said diode illumination source includes at least one diagnostic laser diode light source having a wavelength selected for enhancing a selected feature of said object being viewed.

14. The color video diagnostic system for mini-endoscopes according to claim 12 further comprising:

means for combining light beams from said at least first, second and third laser diode light sources for provision to said optical waveguide means.

15. The color video diagnostic system for mini-endoscopes according to claim 12 wherein said optical waveguide means includes at least one optical fiber.

16. The color video diagnostic system for mini-endoscopes of claim 15, wherein said single optical fiber has a core diameter no greater than 60 μm.

* * * * *